(12) United States Patent
Yanagihara et al.

(10) Patent No.: US 9,328,369 B2
(45) Date of Patent: May 3, 2016

(54) PROCESS FOR PRODUCTION OF USEFUL SUBSTANCE, AND SURFACTANT FOR USE IN THE PROCESS

(75) Inventors: Fusamitsu Yanagihara, Kyoto (JP); Shunichiro Yamaguchi, Kyoto (JP)

(73) Assignee: SANYO CHEMICAL INDUSTRIES, LTD., Kyoto-shi (JP)

( * ) Notice: Subject to any disclaimer, the term of this patent is extended or adjusted under 35 U.S.C. 154(b) by 0 days.

(21) Appl. No.: 13/375,105

(22) PCT Filed: May 26, 2010

(86) PCT No.: PCT/JP2010/058926
§ 371 (c)(1),
(2), (4) Date: Feb. 8, 2012

(87) PCT Pub. No.: WO2010/137624
PCT Pub. Date: Dec. 2, 2010

(65) Prior Publication Data
US 2012/0129220 A1    May 24, 2012

(30) Foreign Application Priority Data

May 29, 2009  (JP) ................................ 2009-131466
Jan. 27, 2010  (JP) ................................ 2010-014937

(51) Int. Cl.
C12P 21/02      (2006.01)
C12N 1/38       (2006.01)
C12P 1/04       (2006.01)

(52) U.S. Cl.
CPC . *C12P 21/02* (2013.01); *C12N 1/38* (2013.01); *C12P 1/04* (2013.01)

(58) Field of Classification Search
None
See application file for complete search history.

(56) References Cited

U.S. PATENT DOCUMENTS

2008/0200358 A1    8/2008  Azuse et al.
2009/0111971 A1*   4/2009  Yamaguchi et al. .......... 530/345
2012/0328543 A1*  12/2012  Mallard et al. ................. 424/61

FOREIGN PATENT DOCUMENTS

FR           2671099 A1      7/1992
JP         2006-002330 A     1/2006
JP         2008-208323 A     9/2008
WO     WO 2004112732 A2 *  12/2004

OTHER PUBLICATIONS

Manderson D. A recombinant vaccine against hydatidosis: production of the antigen in *Escherichia coli*. Journal of Industrial Microbiology and Biotechnology. 2006. 33:173-182.*

International Search Report of PCT/JP2010/058926, mailing date Jul. 27, 2010.
Fernandez, Luis A. et al.; "Specific Secretion of Active Single-Chain Fv Antibodies into the Supernatants of *Escherichia coli* Cultures by Use of the Hemolysin System"; Applied and Environmental Microbiology, vol. 66, No. 11, Nov. 2000, pp. 5024-5029.
Jang, K. H. et al.; "Extracellular secretion of levansucrase from *Zymomonas mobilis* in *Escherichia coli*"; Bioprocess Engineering 21, (1999) , pp. 453-458.
Jeong, Ki Jun et al.; "Excretion of Human β-Endorphin into Culture Medium by Using Outer Membrane Protein F as a Fusion Partner in Recombinant *Escherichia coli*"; Applied and Environmental Microbiology, vol. 68, No. 10, Oct. 2002, pp. 4979-4985.
Li, Yuanyi et al.; "Cloning and hemolysin-mediated secretory expression of a codon-optimized synthetic human interleukin-6 gene in *Escherichia coli*"; Protein Expression and Purification 25, (2002), pp. 437-447.
Rao, J. L. Uma Maheswar et al.; "Enhanced secretion and low temperature stabilization of a hyperthermostable and Ca2+-independent x-amylase of Geobacillus thermoleovorans by surfactants"; Letter in Applied Microbiology, 2003, vol. 36, pp. 191-196.
Reese, E.T. et al.; "Surfactants as Stimulants of Enzyme Production by Microorganisms"; Applied Microbiology, Feb. 1969, vol. 17, No. 2, pp. 242-245.
Van Der Wal et al.; "Optimization of Bacteriocin Release Protein (BRP)-Mediated Protein Release by *Escherichia coli*: Random Mutagenesis of the pCloDF13-Derived BRP Gene to Uncouple Lethality and Quasi-Lysis from Protein Release"; Applied and Environmental Microbiology, vol. 64, No. 2, Feb. 1998, pp. 392-398.
Wan, Eugene W.M. et al.; "TolAIII Co-overexpression Facilitates the Recovery of Periplasmic Recombinant Proteins into the Growth Medium of *Escherichia coli*"; Protein Expression and Purification 14, (1998), Articles No. PT980941, pp. 13-22.
Yang, Junbao et al.; "One Hundred Seventy-Fold Increase in Excretion of an FV Fragment-Tumor Necrosis Factor Alpha Fusion Protein (sFV/TNF-alpha) from *Escherichia coli* Caused by the Synergistic Effects of Glycine and Triton X-100"; Applied and Environmental Microbiology, vol. 64, No. 8, Aug. 1998, pp. 2869-2874.
Tang Jin-Bao et al., "Effect of Glycine and Triton X-100 on secretion and expression of ZZ-EGEP fusion protein"; Food Chemistry, vol. 108, 2008, pp. 657-662.

(Continued)

*Primary Examiner* — David J Steadman
*Assistant Examiner* — Paul Holland
(74) *Attorney, Agent, or Firm* — Westerman, Hattori, Daniels & Adrian, LLP

(57) ABSTRACT

The present invention is aimed to provide a method for industrially producing a useful substance (protein etc.) utilizing a bacterium such as *Escherichia coli* in the presence of a surfactant and a surfactant to be used in this method for producing a useful substance. The present invention is a method for producing a useful substance into a culture solution by secretion by a bacterium in the culture solution, wherein the culture solution contains a surfactant (A), and a dried cell density based on the volume of the culture solution is 1.5 to 500 g/L. More preferably, the present invention is a method for producing a useful substance wherein the surfactant (A) is at least one agent selected from the group consisting of an amphoteric surfactant, an anionic surfactant, and a nonionic surfactant having an HLB value of 0 to 13.

4 Claims, 2 Drawing Sheets

(56) References Cited

OTHER PUBLICATIONS

Wenjuan Yao et al., "Expression and localization of the Corynebacterium glutamicum NCgl1221 protein encoding an L-glutamic acid exporter"; Microbiological Research, vol. 164, 2009, pp. 680-687.

Jun Nakamura et al., "Mutations of the Corynebacterium glutamicum NCgl1221 Gene, Encoding a Mechanosensitive Channel Homolog, Induce I-Glutamic Acid Production"; Applied and Environmental Microbiology, vol. 73, 2007, pp. 4491-4498.

Hiroyuki Mukaiyama et al., "Dextran sodium sulfate enhances secretion of recombinant human transferrin in Schizosaccharomyces pombe"; Applied Microbiology and Biotechnology, vol. 85, 23 Jul. 2009, pp. 155-164.

Umakoshi, H. et al., "Design of Selective Release and Recovery of Enzymes From *Escherichia coli* Based on Their Location Using Nonionic Detergent, Triton X-Series", Trans IChemE, 1998, Vo. 76, Part C, pp. 162-168, cited in European Office Action for dated Jan. 29, 2014 for counterpart EP Appln. No. 10780579.8 (7 pages).

* cited by examiner

SEQUENCE LISTING

```
<160> NUMBER OF SEQ ID NOS: 10

<210> SEQ ID NO 1
<211> LENGTH: 29
<212> TYPE: DNA
<213> ORGANISM: Artificial Sequence
<220> FEATURE:
<223> OTHER INFORMATION: Primer 1

<400> SEQUENCE: 1
attaacatat gaaacaaagc actattgca                                          29

<210> SEQ ID NO 2
<211> LENGTH: 29
<212> TYPE: DNA
<213> ORGANISM: Artificial Sequence
<220> FEATURE:
<223> OTHER INFORMATION: Primer 2

<400> SEQUENCE: 2
attaaggatc cttatttcag ccccagagc                                          29

<210> SEQ ID NO 3
<211> LENGTH: 26
<212> TYPE: DNA
<213> ORGANISM: Artificial Sequence
<220> FEATURE:
<223> OTHER INFORMATION: Primer 3

<400> SEQUENCE: 3
attaacatat gaacaataac gatctc                                             26

<210> SEQ ID NO 4
<211> LENGTH: 30
<212> TYPE: DNA
<213> ORGANISM: Artificial Sequence
<220> FEATURE:
<223> OTHER INFORMATION: Primer 4

<400> SEQUENCE: 4
attaaggatc ctcatgattt cacctgcgac                                         30
```

```
<210> SEQ ID NO 5
<211> LENGTH: 26
<212> TYPE: DNA
<213> ORGANISM: Artificial Sequence
<220> FEATURE:
<223> OTHER INFORMATION: Primer 5

<400> SEQUENCE: 5
attaacatat ggttaaaacc caacgt                                       26

<210> SEQ ID NO 6
<211> LENGTH: 30
<212> TYPE: DNA
<213> ORGANISM: Artificial Sequence
<220> FEATURE:
<223> OTHER INFORMATION: Primer 6

<400> SEQUENCE: 6
attaaggatc ctcattgggt gttaacaatc                                   30

<210> SEQ ID NO 7
<211> LENGTH: 25
<212> TYPE: DNA
<213> ORGANISM: Artificial Sequence
<220> FEATURE:
<223> OTHER INFORMATION: Primer 7

<400> SEQUENCE: 7
taataccatg gcggctcagc cggcg                                        25

<210> SEQ ID NO 8
<211> LENGTH: 26
<212> TYPE: DNA
<213> ORGANISM: Artificial Sequence
<220> FEATURE:
<223> OTHER INFORMATION: Primer 8

<400> SEQUENCE: 8
taataggatc cttattgagc ggcagc                                       26

<210> SEQ ID NO 9
<211> LENGTH: 30
<212> TYPE: DNA
<213> ORGANISM: Artificial Sequence
<220> FEATURE:
<223> OTHER INFORMATION: Primer 9

<400> SEQUENCE: 9
tggatccatg gcgcagctta ccttaaaagg                                   30

<210> SEQ ID NO 10
<211> LENGTH: 27
<212> TYPE: DNA
<213> ORGANISM: Artificial Sequence
<220> FEATURE:
<223> OTHER INFORMATION: Primer 10

<400> SEQUENCE: 10
ctgcaggatc cttatttagg ttcagtg                                      27
```

PROCESS FOR PRODUCTION OF USEFUL SUBSTANCE, AND SURFACTANT FOR USE IN THE PROCESS

TECHNICAL FIELD

The present invention relates to a method for producing a useful substance and a surfactant used in the method. More specifically, the present invention relates to a method for producing a useful substance in which a bacterium secretes the useful substance in the presence of a surfactant, and a surfactant used in the method for producing a useful substance.

BACKGROUND ART

Bacteria are widely used for producing useful substances such as amino acids and proteins. Especially, in recent years, there has been proposed an art in which a useful protein is efficiently produced using a bacterium transformed by genes of a medically- or industrially-useful protein introduced thereinto by genetic engineering techniques.

A bacterium commonly used for protein expression is *Escherichia coli* that is a gram negative bacterium. The art utilizing *Escherichia coli* in protein expression has been developed and the art is widely used in production of proteins for industrial, food processing, and medical purposes.

Examples of a method of extracting a protein expressed by using *Escherichia coli* include physical fracturing methods such as ultrasonication, a method using a high-pressure homogenizer or french press. Such techniques are widely applied in practice. In these physical fracturing methods, *Escherichia coli* cells are killed when the protein is extracted.

Accordingly, the following methods are effective to increase the amount of the protein to be obtained:

1. Increasing the amount of a recombinant protein expressed per cell; and
2. Increasing the number of cells.

However, the following disadvantages are found in the physical fracturing methods of extracting a recombinant protein from *Escherichia coli* by breaking *Escherichia coli*.

1. Equipment for fracturing *Escherichia coli* is needed.
2. Nucleic acid constituents such as genomic DNA simultaneously extracted need to be removed from protein extracts for progress of purification, because the nucleic acid constituents may increase a viscosity of the protein extracts.
3. A large amount of proteins derived from *Escherichia coli* and other impurities contaminated in the protein extracts may cause toxicity and immunogenicity.
4. Purification process is needed in which a large amount of contaminated proteins derived from *Escherichia coli* is isolated from a recombinant protein.
5. Accumulation of a recombinant protein in *Escherichia coli* limits the production volume.
6. Inclusion bodies are formed in cells of a bacteria.
7. A required amount of a recombinant protein is not expressed because the recombinant protein is degraded by proteases.

To overcome these disadvantages, a method in which *Escherichia coli* secretes a recombinant protein in a culture solution is needed.

Extracytoplasmic expression of a recombinant protein by *Escherichia coli* is commonly carried out by fusing a signal sequence required for inner membrane translocation to a target recombinant protein. Examples of the signal sequence required for inner membrane translocation include signal sequences derived from PelB, OmpA, StII, PhoA, OmpF, PhoE, MalE, OmpC, Lpp, LamB, OmpT, LTB, TorA, and the like, and signal sequences derived from endoxylanase and the like derived from *Bacillus*. The recombinant protein fused with such a signal sequence is translocated to a periplasm via a Sec pathway or a TAT pathway of an inner membrane translocation mechanism provided in *Escherichia coli*. However, since a peptidoglycan layer and an outer membrane are provided outside the inner membrane of *Escherichia coli*, the recombinant protein are commonly not secreted into the culture solution.

Non Patent Documents 1 to 7 each disclose a production method of a recombinant protein by secretion into a culture solution.

The methods disclosed in the above Non Patent Documents each have at least one of the following disadvantages.

1. Since *Escherichia coli* easily dies, the method does not suit for high-density or continuous production.
2. The method only suits for production of a specific recombinant protein.
3. Since the recombinant protein is expressed as a fusion protein with a membrane protein and the like, the fusion protein may affect the expression of the activity. Accordingly, the process for cutting the fusion protein is needed, which raises costs.
4. The expression amount of the recombinant protein is not adequate.

Non Patent Document 1: Jang et al., Bioproc. Eng., 21 (1999) 453-458

Non Patent Document 2: Yang et al., Appl. Environ. Microbiol., 64 (1998) 2669-2874

Non Patent Document 3: Jeong et al., Appl. Environ. Microbiol., 68 (2002) 4979-4985

Non Patent Document 4: Van der Wal et al., Appl. Environ. Microbiol., 64 (1998) 392-398

Non Patent Document 5: Wan et al., Protein Expr. Purif., 14 (1998) 13-22

Non Patent Document 6: Fernandez et al., Appl. Environ. Microbiol., 66 (2000) 5024-5029

Non Patent Document 7: Li et al., Gene, 25 (2002) 437-447

DISCLOSURE OF THE INVENTION

Problems to be Solved by the Invention

The present invention is aimed to provide a method for industrially producing a useful substance (protein, etc.) utilizing a bacterium such as *Escherichia coli* in the presence of a surfactant, and a surfactant used in this method for producing a useful substance.

Means for Solving the Problems

The present inventors have made intensive studies to achieve the above purpose and have arrived at the present invention.

Namely, the present invention is a method for producing a useful substance into a culture solution by secretion by a bacterium in the culture solution, wherein the culture solution contains a surfactant (A), and a dried cell density based on the volume of the culture solution is 1.5 to 500 g/L, and a surfactant used in this method for producing a useful substance.

Effect of the Invention

The present invention exerts the following effects.

The method for producing a useful substance of the present invention allows high-volume production of a useful substance.

Additionally, addition of the surfactant of the present invention in production of a useful substance (protein, etc.) utilizing a bacterium increases the production volume and the secretion amount.

MODES FOR CARRYING OUT THE INVENTION

Figure 1:
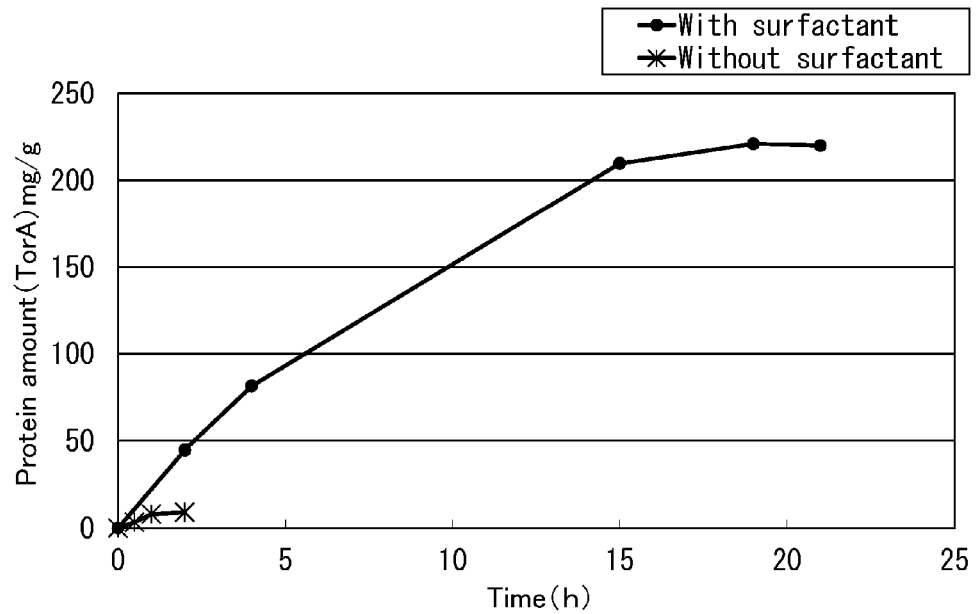
FIG. 1 is a graph showing the time course of protein production per gram of bacterial cells with regard to the results of Comparative Example 1 and Example 1.

The method for producing a useful substance of the present invention is a method for producing a useful substance into a culture solution by secretion by a bacterium in the culture solution, wherein the culture solution contains a surfactant (A), and a dried cell density based on the volume of the culture solution is 1.5 to 500 g/L.

Examples of the bacterium in the present invention include, but not limited to, eubacteria and archaebacteria. The eubacteria include gram negative bacteria and gram positive bacteria. The gram negative bacteria include *Escherichia, Thermus, Rhizobium, Pseudomonas, Shewanella, Vibrio, Salmonella, Acetobacter*, and *Synechocystis*. The gram positive bacteria include *Bacillus, Streptmyces, Corynebacterium, Brevibacillus, Bifidobacterium, Lactococcus, Enterococcus, Pediococcus, Leuconostoc*, and *Streptomyces*.

Among these, the gram negative bacteria are preferable from the standpoint of the productivity of the useful substance. Further, *Escherichia* is more preferable and *Escherichia coli* is still more preferable.

The useful substance in the present invention is not particularly limited, and may be proteins (enzyme, hormonal protein, antibody, peptide, etc.), oligosaccharides, nucleic acids, and the like.

Examples of the proteins include enzymes {oxidoreductase (cholesterol oxidase, glucose oxidase, ascorbate oxidase, peroxidase, etc.), hydrolase (lysozyme, protease, serine protease, amylase, lipase, cellulase, glucoamylase, etc.), isomerase (glucose isomerase, etc.), transferase (acyl transferase, sulfotransferase, etc.), synthase (fatty acid synthase, phosphate synthase, citrate synthase, etc.), lyase (pectin lyase, etc.), etc.}, hormonal proteins {bone morphogenetic protein (BMP), interferon α, interferon β, interleukins 1 to 12, growth hormone, erythropoietin, insulin, granulocyte-colony stimulating factor (G-CSF), tissue plasminogen activator (TPA), natriuretic peptide, coagulation factor VIII, somatomedin, glucagon, growth hormone releasing factor, serum albumin, calcitonin, etc.}, antibody {single-chain antibody, IgG large subunit, IgG small subunit, etc.}, antigenic protein {hapatitis B surface antigen, etc.}, functional protein {Pronectin (registered trade mark), anti-freeze peptide, anti-bacterial peptide, etc.}, fluorescent protein (GFP, etc.), luminescent protein (luciferase, etc.), and peptide (amino acid composition not particularly limited:oligopeptide, dipeptide, tripeptide, etc.).

Examples of the oligosaccharides include sucrose, lactose, trehalose, maltose, raffinose, panose, cyclodextrin, galactooligosaccharides, and fructooligosaccharides.

Examples of the nucleic acids include inosine monophosphate, adenosine monophosphate, and guanosine monophosphate.

Among these useful substances, proteins are preferable and enzymes and hormonal proteins are more preferable, from the standpoint of easy production of the useful substance.

In the case that the useful substance is a protein, the protein is preferably partly or entirely translocatable to a periplasm after being expressed in a bacterium. Moreover, the protein preferably encodes a signal sequence needed for translocation to a periplasm in ORF.

The periplasm refers to a space between the cell membrane of a bacterium and the top surface of the bacterium.

Examples of the signal sequence needed for translocation to a periplasm include a Sec secretion signal sequence and a TAT secretion signal sequence.

The surfactant (A) used in the method for producing a useful substance of the present invention is at least one surfactant selected from the group consisting of an amphoteric surfactant (A1), an anionic surfactant (A2), a nonionic surfactant (A3), and a cationic surfactant (A4).

Examples of the amphoteric surfactant (A1) include a carboxylate-type amphoteric surfactant (A1-1), a sulfate-type amphoteric surfactant (A1-2), a sulfonate-type amphoteric surfactant (A1-3), and a phosphate-type amphoteric surfactant (A1-4).

Examples of the carboxylate-type amphoteric surfactant (A1-1) include an amino acid-type amphoteric surfactant (A1-1-1), a betaine-type amphoteric surfactant (A1-1-2), and an imidazoline-type amphoteric surfactant (A1-1-3).

The amino acid-type amphoteric surfactant (A1-1-1) is an amphoteric surfactant having an amino group and a carboxyl group in the molecule, and is exemplified by a compound represented by the following formula (1):

$$[R-NH-(CH_2)_n-COO^-]_m M \qquad (1).$$

In the formula (1), R represents a C1-C20 monovalent hydrocarbon group, n represents an integer of 1 or larger, m represents an integer of 1 or larger, and M represents proton or a monovalent or divalent cation such as an alkali metal, an alkaline earth metal, ammonium (including cation derived from amine, alkanolamine, or the like), and quaternary ammonium.

Specific examples of the surfactant (A1-1-1) include alkylamino propionate type amphoteric surfactants (e.g. sodium cocaminopropionate, sodium stearylaminopropionate, and sodium lauryl amino propionate, etc.); alkyl aminoacetate amphoteric surfactants (sodium lauryl aminoacetate, etc.), and sodium N-lauroyl-N'-carboxymethyl-N'-hydroxyethylethylenediamine.

The betaine-type amphoteric surfactant (A1-1-2) is an amphoteric surfactant having a quaternary ammonium salt-type cationic part and a carboxylate-type anionic part in the molecule, and is exemplified by a compound represented by the following formula (2):

Specific examples of the surfactant (A1-1-2) include alkyl dimethyl betaine (stearyldimethylaminoacetatebetaine, lauryl dimethylaminoacetatebetaine, etc.), amide betaine (palm oil fatty acid amide propyl betaines (palm oil fatty acid amide propyl dimethyl aminoacetatebetaine, etc.), lauricacid amide propyl betaine, etc.), alkyl dihydroxy alkyl betaine (lauryl dihydroxyethylbetaine, etc.), and cured palm oil fatty acid amide propyl dimethyl aminoacetatebetaine.

$$R\text{—}N^+(CH_3)_2\text{—}CH_2COO^- \quad (2).$$

In the formula (2), R represents a C1-C20 monovalent hydrocarbon group.

Examples of the imidazoline-type amphoteric surfactant (A1-1-3) include 2-alkyl-N-carboxymethyl-N-hydroxyethyl imidazoliniumbetaine.

Other amphoteric surfactants include: glycine-type amphoteric surfactants such as sodium lauroyl glycine, sodium lauryl diaminoethyl glycine, lauryl diaminoethyl glycine hydrochloride, and dioctyldiaminoethyl glycine hydrochloride; sulfobetaine-type amphoteric surfactants such as pentadecylsulfotaurine; cholamidopropyldimethylammoniopropanesulfonate (CHAPS), and cholamidopropyldimethylammoniohydroxylpropanesulfonate (CHAPSO); and alkylamine oxide-type amphoteric surfactants such as lauryldimethylamine oxide.

Examples of the anionic surfactants (A2) include ether carboxylic acids (A2-1) and its salts, sulfate ester (A2-2) and its salts, ether sulfate ester (A2-3) and its salts, sulfonate (A2-4), sulfosuccinate (A2-5), phosphate ester (A2-6) and its salts, ether phosphate ester (A2-7) and its salts, fatty acid salts (A2-8); naturally-derived carboxylic acid and its salts (e.g. chenodeoxycholic acid, cholic acid, deoxycholic acid, etc.), and acylated amino acid salts.

The ether carboxylic acid (A2-1) and its salts include ether carboxylic acid having a C8-C24 hydrocarbon group and its salts. Specific examples thereof include polyoxyethylene lauryl ether acetate, sodium polyoxyethylene lauryl ether acetate, sodium polyoxyethylenetridecyl ether acetate, sodium polyoxyethyleneoctyl ether acetate, and sodium lauryl glycol acetate.

The sulfate ester (A2-2) and its salt include sulfate ester having a C8-C24 hydrocarbon group and its salt. Specific examples thereof include sodium lauryl sulfate and triethanolamine lauryl sulfate.

The ether sulfate ester (A2-3) and its salt include ether sulfate ester having a C8-C24 hydrocarbon group and its salt. Specific examples thereof include sodium polyoxyethylenelaurylether sulfate and triethanolaminepolyoxyethylenelaurylether sulfate.

Examples of the sulfonate (A2-4) include sodium dodecyl diphenyl ether disulfonate, sodium dodecylbenzenesulfonate, and sodium naphthalenesulfonate.

Examples of the sulfosuccinate (A2-5) include disodium polyoxyethylene lauryl sulfosuccinate, disodiumlauryl sulfosuccinate, and disodium polyoxyethylenelauroylethanolamidesulfosuccinate.

Examples of the phosphate ester (A2-6) include disodium octyl phosphate and disodium lauryl phosphate.

Examples of the ether phosphate ester (A2-7) include disodium polyoxyethyleneoctyl ether phosphate and disodium polyoxyethylene lauryl ether phosphate.

Examples of the fatty acid salt (A2-8) include sodium octoate, sodium laurate, and sodium stearate.

Examples of the nonionic surfactant (A3) include alcohol alkylene oxide (hereinafter, alkylene oxide is abbreviated as AO) adducts (A3-1), alkylphenol AO adducts (A3-2), fatty acid AO adducts (A3-3), and polyalcohol type nonionic surfactants (A3-4).

HLB is known as a measure of hydrophilicity and hydrophobicity of a nonionic surfactant. A higher HLB value indicates higher hydrophilicity. The HLB value in the present invention is calculated by using the following formula (1) (Takehiko FUJIMOTO, Kaimenkasseizainyumon (Introduction to Surfactants), page 142, published by Sanyo Chemical Industries, Ltd.).

$$HLB = 20 \times \{\text{molecular mass of hydrophilic group/molecular mass of surfactant}\} \quad (1)$$

The HLB value of the nonionic surfactant (A3) is preferably 0 to 13, more preferably 5 to 12, and still more preferably 8 to 12, from the standpoint of secretion efficiency.

Examples of the alcohol AO adducts (A3-1) include polyoxyethylenealkylether and polyoxyalkylenealkylether. Specific examples thereof include adducts (including block adducts and/or random adducts: the same shall apply in the following cases) of 0 to 20 mol of ethylene oxide (hereinafter, ethylene oxide is abbreviated as EO) and/or 1 to 20 mol of propylene oxide (hereinafter, propylene oxide is abbreviated as PO) of C8-C24 higher alcohols (decyl alcohol, dodecyl alcohol, palm oil alkyl alcohol, octadecyl alcohol, oleyl alcohol, etc.) (for example block adduct of EO 8 mol/PO 7 mol of decyl alcohol). More specifically, examples thereof include 7 mol EO adducts of lauryl alcohol (HLB=12.4), 5 mol EO adducts of oleyl alcohol (HLB=9.0), 6 mol EO adducts of oleyl alcohol (HLB=10.2), 7 mol EO adducts of oleyl alcohol (HLB=11.0), 10 mol EO adducts of oleyl alcohol (HLB=12.4), and 1,2-dodecandiol monooxyethylene adducts.

The alkylphenol AO adducts (A3-2) include an alkylphenol AO adduct having a C6-C24 alkyl group. Specific examples thereof include 1-20 mol EO and/or 1-20 mol PO adducts of octyl phenol and a 1-20 mol EO and/or 1-20 mol PO adducts of nonyl phenol. TRITON™X-114 (HLB=12.4), Igepal™CA-520 (HLB=10.0), and Igepal™CA-630 (HLB=13.0) are readily available from the market.

The fatty acid AO adducts (A3-3) include 1-20 mol EO and/or 1-20 mol PO adducts of C8-C24 fatty acids (decanoic acid, lauric acid, myristic acid, palmitic acid, stearic acid, oleic acid, palm oil fatty acid, etc.). Specific examples thereof include 9 mol EO adducts of oleic acid (HLB=11.8), 12 mol EO adducts of dioleic acid (HLB=10.4), 20 mol EO adducts of dioleic acid (HLB=12.9), and 9 mol EO adducts of stearic acid (HLB=11.9).

The polyalcohol nonionic surfactants (A3-4) include: EO and/or PO adducts of C3-C36 polyvalent (divalent to octavalent) alcohols (glycerine, trimethylolpropane, pentaerythritol, sorbit, sorbitan, etc.); fatty acid esters of the polyvalent alcohol and their EO adducts; and fatty acid esters and fatty acid alkanolamides of sucrose (palm oil fatty acid diethanol amide, etc.) and their AO adducts. Specific examples thereof include EO adducts of sorbitantetraoleate (HLB=11.4) and EO adducts of sorbitanhexaoleate (HLB=10.2).

The cationic surfactants (A4) include an amine salt-type cationic surfactant (A4-1) and a quaternary ammonium salt-type cationic surfactant (A4-2).

The amine salt-type cationic surfactants (A4-1) include primary to tertiary amines neutralized by an inorganic acid (hydrochloric acid, nitric acid, sulfuric acid, hydroiodic acid, etc.) or organic acid (acetic acid, formic acid, oxalic acid, lactic acid, gluconic acid, adipic acid, alkyl phosphate, etc.). Examples of the primary amine salt type include: inorganic or organic salts of aliphatic higher amines (higher amines such as lauryl amine, stearyl amine, cetyl amine, cured tallow amine, and rosin amine); and higher fatty acid (stearic acid, oleic acid, etc.) salt of lower amines. Examples of the secondary amine salt type include inorganic or organic salts of ethylene oxide adducts of aliphatic amines. Examples of the tertiary amine salt type include aliphatic amines (triethylamine, ethyldimethylamine, N,N,N',N'-tetramethylethylenediamine, etc.), ethyleneoxide (2 mol or more) adducts of aliphatic amines, alicyclic amines (N-methylpyrrolidine, N-methylpiperidine, N-methylhexamethyleneimine, N-methylmorpholine, 1,8-dizabicyclo(5,4,0)-7-undecene, etc.), inorganic or organic salts of nitrogen-containing heterocyclic aromatic amines (4-dimethylaminopyridine, N-methylimidazole, 4,4'-dypyridyl, etc.), and inorganic or organic salts of tertiary amines such as triethanolaminemonostearate and stearamideethyldiethylmethylethanolamine.

Examples of the quaternary ammonium salt-type cationic surfactant (A4-2) include ones obtainable by a reaction between tertiary amines and quaternarizing agents (alkylating agents such as methylchloride, methyl bromide, ethyl chloride, benzyl chloride, dimethylsulfuric acid; ethylene oxide, etc.). Examples thereof include lauryl trimethyl ammonium chloride, didecyl dimethyl ammonium chloride, dioctyl dimethyl ammonium bromide, stearyltrimethyl ammonium bromide, lauryl dimethyl benzyl ammonium chloride (benzalkonium chloride), cetylpyridinium chloride, polyoxyethylenetrimethyl ammonium chloride, and stearamideethyldiethylmethyl ammonium methosulfate.

The surfactant (A) is preferably an amphoteric surfactant, an anionic surfactant, or a nonionic surfactant having an HLB value of 0 to 13, from the standpoint of secretion efficiency. More preferably, the surfactant (A) is a carboxylate-type amphoteric surfactant (A1-1), an ether carboxylic acid (A2-1), a sulfonate (A2-4), a higher alcohol AO adduct (A3-1), or a polyalcohol type nonionic surfactant (A3-4). A particularly preferable surfactant (A) is sodium polyoxyethylenetridecylether acetate (sodium salt of polyoxyethylenetridecyl ether acetate (A2-1)), palm oil fatty acid diethanol amide (A3-4), palm oil fatty acid amide propyl dimethyl aminoacetatebetaine (A1-1-2), a 1,2-dodecandiol monooxyethylene adduct (A3-1), lauryl dimethylaminoacetatebetaine (A1-1-2), cured palm oil fatty acid amidopropyl dimethyl aminoacetatebetaine (A1-1-2), sodium cocaminopropionate (A1-1-1), sodiumdodecyl diphenyl ether disulfonate (A2-4), sodium polyoxyethylenelaurylether acetate (sodium salt of polyoxyethylenelaurylether acetate (A2-1)), a higher alcohol EO adduct (A3-1), sodium polyoxyethylenelaurylether sulfate (sodium salt of polyoxyethylenelaurylether sulfate (A2-3)), or a decyl alcohol EO adduct (A3-1).

The surfactant (A) in the present invention may be used as it is or may be mixed with water to be used in the form of an aqueous diluted solution (in the form of aqueous solution or aqueous dispersion) according to need.

The total concentration of the surfactant (A) in the aqueous diluted solution may be determined as appropriate in accordance with the target microorganism, the kind of a bioactive substance, and the method of extraction. From the standpoint of secretion and handleability of the useful substance, the total concentration of the surfactant (A) is preferably 0.1% to 99% by weight and more preferably 1% to 50% by weight on the basis of the weight of the aqueous diluted solution.

The secretion efficiency (%) when a useful substance is produced by using the surfactant of the present invention is preferably 1 to 100, more preferably 5 to 100, still more preferably 10 to 100, and particularly preferably 50 to 100 from the standpoint of the productivity of the useful substance.

The secretion efficiency of the surfactant indicates that the surfactant makes the useful substance in a bacterium to be secreted outside the bacterium (into the culture solution).

In the present invention, the secretion efficiency is determined by the following formula:

$$\text{Secretion efficiency (\%)} = 100 \times \{(X/Y) - Z\}.$$

In the formula, "X" represents a useful substance in the culture solution which remains after removal of bacterial cells by centrifugation.

"Y" represents the whole useful substance in the culture solution.

"Z" represents the ratio of lysed bacteria determined by the following formula:

$$Z = Z1/Z2.$$

In the formula, "Z1" represents intracytoplasmic localized substance in the culture solution which remains after removal of bacterial cells by centrifugation.

"Z2" represents the whole intracytoplasmic localized substance in the culture solution.

Here, the intracytoplasmic localized substance refers to a substance that is present inside the cytoplasm and is eluted in the culture solution by bacteriolysis.

The secretion efficiency is increased when more protein produced in a bacterium is translocated to a periplasm, and is decreased when less protein produced in a bacterium is translocated to a periplasm. Moreover, screening may be carried out to select a surfactant having high secretion efficiency for increasing the secretion efficiency.

The amount (% by weight) of the surfactant (A) used in the method for producing a useful substance of the present invention is appropriately determined in accordance with the target microorganism, the kind of a useful substance to be produced and the method of extraction. From the standpoint of secretion efficiency and less tendency to cause protein denaturation, the amount of the surfactant (A) is preferably 0.0001 to 10, more preferably 0.005 to 10, and still more preferably 0.1 to 5, on the basis of the weight of the culture solution.

The surfactant (A) may be previously mixed with the culture solution or added later to the culture solution in which a microorganism is suspended. The surfactant (A) may be added to the culture solution at a temperature of 4° C. to 99° C. and may be stirred with a stirring blade or stirrer to be mixed with the culture solution. To be mixed later with the culture solution, the surfactant (A) may be added while stirring with a stirring blade or the like.

One of the above listed surfactants (A) may be used solely or a plurality of them may be used in combination.

The dried cell density in the present invention refers to the weight of the bacteria contained in 1 L of the culture solution at any time point during the culturing from its initiation to completion, in the production of a useful substance by secretion. Here, the weight of the bacteria refers to the weight of the dried bacteria.

The dried cell density is determined by the following processes (1) to (5):

(1) measuring the weight of the container (centrifuge tube) in advance;

(2) charging 100 ml of a culture solution into the container weighed in the process (1), centrifuging the culture solution (4000 G, 15 minutes, 4° C.), and collecting the bacteria by removing the supernatant;

(3) washing the collected bacteria with a 0.9 wt % NaCl aqueous solution [same volume as the culture solution used in the process (2)], centrifuging the solution again (4000 G, 15 minutes, 4° C.), and collecting the bacteria by removing the supernatant;

(4) drying the bacteria obtained in the process (3) in the container at 105° C. for 10 hours, and measuring the total weight of the container and the bacteria; and (5) further drying the bacteria at 105° C. for 2 hours after the process (4) and measuring the total weight of the container and the bacteria to confirm that no weight change is observed, and if the weight is further reduced, continuing the drying at 105° C. until the weight change is not observed.

The dried cell density is determined by applying the measuring results in the process (5) and the process (1) and the volume (L) of the culture solution used in the process (2) to the following formula:

Dried cell density (g/L)=([measuring result in process (5)]−[measuring result in process (1)])/0.1.

The dried cell density in the method for producing a useful substance of the present invention is 1.5 to 500 g/L, preferably 3 to 200 g/L, and more preferably 4 to 100 g/L, on the basis of the volume of the culture solution. When the dried cell density is less than 1.5 g/L, the productivity of a useful substance is lowered. When the dried cell density is more than 500 g/L, a useful substance is hardly produced.

The dried cell density when the bacterium is *Escherichia coli* is 1.5 to 500 g/L, preferably 3 to 100 g/L, more preferably 10 to 50 g/L, and most preferably 12 to 27 g/L, on the basis of the volume of the culture solution, from the standpoint of the productability of a useful substance.

In the method for producing a useful substance of the present invention, larger dried cell density enables production of a useful substance in a larger volume, provided that the dried cell density is within the above range.

In the method for producing a useful substance of the present invention, the time period during which the dried cell density is within the above range is preferably 10% or more and more preferably 50% or more of the time period required for secretion of a useful substance, from the standpoint of the production volume of a useful substance.

The dried cell density can be increased by performing appropriate fed-batch operation of a fed-batch culture method under a sufficient aeration condition. In contrast, the dried cell density can be decreased by performing batch culture under a limited aeration condition. Moreover, the dried cell density can be increased by lengthening the time period from the initiation of culturing to addition of the surfactant and can be decreased by shortening the time period from the initiation of culturing to addition of the surfactant. Further, the dried cell density can be increased by lowering the charging speed of the surfactant and can be decreased by increasing the charging speed of the surfactant.

In the method for producing a useful substance of the present invention, the method for producing a useful substance by secretion includes production by extracellular secretion having the processes (a) and (b). In the following processes, secretion is carried out in the process (a).

The processes include:

(a) allowing the culture solution to culture the bacterium (gram negative bacterium, etc.) for producing a useful substance and the surfactant to coexist to secrete the useful substance extracellularly (into the culture solution); and (b) isolating the useful substance from the culture solution after the process (a).

Exemplary methods for producing a useful substance with use of a surfactant of the present invention are shown below.

(i) Gene Recombination (i-1) A messenger RNA (mRNA) is isolated from a cell expressing a target protein. A single-chain cDNA is synthesized from the mRNA and then a double-chain DNA is synthesized. The double-chain DNA is incorporated in a phage DNA or plasmid. The obtained recombinant phage or plasmid is transformed into host *Escherichia coli* to form a cDNA library.

(i-2) Examples of a method of screening a phage DNA or plasmid containing a target DNA include hybridization of a phage DNA or plasmid with a target protein gene or DNA probe encoding a part of the complementary sequence.

(i-3) A cloned target DNA or a part thereof is cut out from the phage or plasmid after screening. The cloned DNA or a part thereof is connected to a site downstream to the promoter in an expression vector. In this manner, an expression vector of the target gene is formed. A DNA encoding a signal sequence for translocating the inner membrane (signal sequence for expressing the target substance in the periplasm) can be connected at the same time.

(ii) Culture (ii-1) A host bacterium is transformed with an expression vector to form a recombinant bacterium. The recombinant bacterium is preliminary cultured on an agar medium commonly at 15° C. to 43° C. for 3 to 72 hours.

(ii-2) Autoclave sterilization is performed on a culture solution to be used for production of a useful substance at 121° C. for 20 minutes. The recombinant bacterium preliminary cultured on the agar medium is cultured in this culture solution. Culturing is curried out commonly at 15° C. to 43° C. for 12 to 72 hours. When the surfactant (A) is used concurrently with the initiation of culturing, a solution obtained by mixing the surfactant (A) and the culture solution and uniforming the mixture is used as a culture solution and the same operation is performed. When the surfactant (A) is added after 6 to 72 hours from the initiation of culturing, the culturing is kept going for 1 to 1000 hours after addition of the surfactant.

(iii) Purification (iii-1) Protein secreted into the culture solution is isolated from microorganisms and residual microorganisms by centrifugation, hollow fiber membrane separation, filtration, or the like.

(iii-2) A column chromatography such as ion-exchange column chromatography, gel filtration column chromatography, hydrophobic column chromatography, affinity column chromatography, and extra column chromatography is repeatedly performed on the culture solution containing protein. Precipitation such as ethanol precipitation, ammonium sulfate precipitation, and polyethyleneglycol precipitation is appropriately performed according to need. In this manner, isolation and purification are conducted.

The host bacterium isolated in (iii-1) can be further cultured with additional supply of a culture solution. The culture solution and the like may be further subjected to the process (iii). In this manner, purification and culturing are repeatedly performed so that a useful substance may be produced continuously.

Examples of fillers used in column chromatography in the procedure of isolation and collecting of protein in the process (iii) include silica, dextran, agarose, cellulose, acrylamide, and vinyl polymer. Commercially-available products thereof include Sephadex series, Sephacryl series, Sepharose series (all produced by Pharmacia Ltd.) and Bio-Gel series (produced by Bio-Rad Laboratories Inc.).

Use of the method for producing a useful substance of the present invention allows a high yield in a short time, resulting in a large production volume. Additionally, in the method for producing a useful substance of the present invention, the useful substance is secreted into the culture solution. Accordingly, the useful substance is easily purified.

The useful substance obtainable by the production method of the present invention is obtained through the above procedure. Accordingly, the useful substance has higher specific activity than conventional ones.

The method for producing a useful substance of the present invention has a process of having the bacterium and the surfactant coexist to secrete a useful substance into the culture solution. Presumably, in this process, the bacterium can keep producing a useful substance to secrete the useful substance into the culture solution as long as the bacterium is present. Moreover, provided that the bacterium has an ability to produce a useful substance, the production method of the present invention is presumably applicable regardless of the kind of the useful substance to be produced.

The method for producing a useful substance of the present invention is particularly effective when the useful substance produced in the bacterium is translocated in the periplasm of the bacterium. Translocation of the useful substance into the periplasm facilitates secretion of the useful substance into the culture solution.

Another aspect of the present invention is a surfactant used in the method for producing a useful substance of the present invention.

The surfactant of the present invention is added when a useful substance (protein, etc.) is produced with use of a bacterium.

The surfactant of the present invention is less likely to kill the bacterium so that the bacterium can produce a useful substance continuously. As a result, the production volume is significantly increased.

Culturing of a bacterium with use of the surfactant of the present invention allows culturing without killing the bacterium. Accordingly, it is possible to achieve a sufficient cell density for industrial production and to produce a useful substance by secretion. As a result, easy purification and a large production volume are achieved.

The surfactant of the present invention is the surfactant (A) described above.

EXAMPLES

The present invention is described in more detail with reference to the following examples and comparative examples. However, the present invention is not limited to these. Here, it is to be noted that "parts" refers to "parts by weight" unless otherwise indicated.

Common methods known to the person skilled in the art were employed to conduct formation of strains, measurement of the weight of bacterial cells, ELISA assay, SDS-PAGE, and the like.

Production Example 1

An alkaline phosphatase (phoA) gene of an *Escherichia coli* strain W3110 was amplified by the PCR method using primers 1 and 2 (Table 4). After being treated with restriction enzymes NdeI and BamHI, a PCR fragment was bound with an NdeI restriction enzyme site and with a BamHI restriction enzyme site of a pET-22b plasmid (product of Novagen). Then, the plasmid was transformed into an AG1 (DE3) *Escherichia coli* strain formed by transforming an *Escherichia coli* strain AG1 (product of TOYOBO Co., LTD.) with use of a λDE3 Lysogenization Kit (product of Novagen). In this manner, an alkaline phosphatase expressing strain (α) was formed. Localization of the expressed alkaline phosphatase in a periplasmic fraction was confirmed by conducting an analysis based on a method disclosed in page 121 of Vol. 353 of METHODS IN ENZYMOLOGY (2002).

Production Example 2

A torA gene of an *Escherichia coli* strain W3110 was amplified by the PCR method using primers 3 and 4 (Table 4). After being treated with restriction enzymes NdeI and BamHI, a PCR fragment was bound to an NdeI restriction enzyme site and a BamHI restriction enzyme site of a pET-22b plasmid (product of Novagen). Then, the plasmid was transformed into an AG1 (DE3) *Escherichia coli* strain to form a TorA expressing strain (β). Localization of the expressed TorA in a periplasmic fraction was confirmed by conducting an analysis based on the method disclosed in page 121 of Vol. 353 of METHODS IN ENZYMOLOGY (2002).

Production Example 3

A pdxA gene of an *Escherichia coli* strain W3110 was amplified by the PCR method using primers 5 and 6 (Table 4). After being treated with restriction enzymes NdeI and BamHI, a PCR fragment was bound to an NdeI restriction enzyme site and a BamHI restriction enzyme site of a pET-22b plasmid (product of Novagen). Then, the plasmid was transformed into an AG1 (DE3) *Escherichia coli* strain to form a PdxA expressing strain (γ). Localization of the expressed PdxA in a cytoplasmic compartment was confirmed by conducting an analysis based on the method disclosed in page 121 of Vol. 353 of METHODS IN ENZYMOLOGY (2002).

<Screening of Secretion Efficiency>
<A-0>

The secretion efficiency of *Escherichia coli* (α) and (β) in the case of using no surfactant was determined by the processes (1) to (4).

(1) *Escherichia coli* (α), (β), and (γ) obtained in Production Examples 1 to 3 were each inoculated in 1 mL of an LB culture solution (10 g/L of bactotrypton, 5 g/L of yeast extract, 10 g/L of NaCl, 30 mg/L of chloramphenicol) and were shake-cultured at 37° C. overnight. In this manner, culture solutions were prepared.

(2) The strains were collected using a centrifuge (4,000 G, 4° C., 15 minutes). Each of the collected *Escherichia coli* strains was resuspended in 1 mL of a TB culture solution (product of Difco) and chloramphenicol (30 mg/L) and IPTG (100 μM) were added thereto. Shake culture at 37° C. for 3 hours induced expression of phoA, torA, and pdxA.

(3) Subsequently, harvesting using a centrifuge was carried out again (4,000 G, 4° C., 15 minutes). Each of the collected *Escherichia coli* strains was resuspended in 2.5 mL of a Tris-NaCl buffer solution (50 mM Tris (pH 7.5), 100 mM NaCl). The resulting solution was divided into 25-μL portions at a time to be mixed with 25 μL of a Tris-NaCl buffer solution.

(4) Then, the solution was allowed to stand at 37° C. for 1 hour. The supernatant solution was collected and diluted in a Tris-NaCl buffer solution to a proper concentration. Here, the quantification of the recombinant protein in the resulting solution was carried out by ELISA assay with use of an anti-His-tag antibody. The sample prior to the centrifugation in the process (3) was treated with ultrasonic waves (200 W, 10 minutes) and the quantification of the recombinant protein therein was similarly carried out by ELISA assay with use of an anti-His-tag antibody. The ratio of lysed bacteria was obtained with use of *Escherichia coli* (γ), and the secretion efficiencies of the recombinant proteins of *Escherichia coli*

(α) and (β) were calculated by using the following formula. Table 1 shows the results. Here, in Table 1, "0" indicates that the secretion efficiency was 0% and "–" indicates that the secretion efficiency was not measured.

Secretion efficiency (%)=100×{(X/Y)−Z}.

In the formula, "X" represents the amount of the recombinant protein in the culture solution after removal of bacterial cells by centrifugation in the case of using *Escherichia coli* (α) or (β).

"Y" represents the amount of the whole recombinant protein in the culture solution in the case of using *Escherichia coli* (α) or (β).

"Z" represents the ratio of lysed bacteria obtained with use of *Escherichia coli* (γ), which is determined by the following formula:

Z=Z1/Z2.

In the formula, "Z1" represents the amount of the recombinant protein in the culture solution which remains after removal of bacterial cells by centrifugation in the case of using *Escherichia coli* (γ).

"Z2" represents the amount of the whole recombinant protein in the culture solution in the case of using *Escherichia coli* (γ).

<Measurement of Secretion Efficiency of *Escherichia coli* (α)>

"X" represents a measurement value of the amount of the recombinant protein and was 0.0 in the processes (1) to (4) carried out using *Escherichia coli* (α). In the processes, the supernatant solution collected in the process (4) was diluted with a Tris-NaCl buffer solution to an appropriate concentration and the amount of the recombinant protein therein was obtained by ELISA assay (using a spectro photometer "SUN-RISE THERMO" produced by Wako Pure Chemicals Industries) with use of an anti-His-tag antibody.

"Y" represents a measurement value of the amount of the recombinant protein and was 2.5 in the processes (1) to (4) carried out using *Escherichia coli* (α). In the processes, the sample prior to the centrifugation in the process (β) was treated with ultrasonic waves (200 W, 10 minutes) and the amount of the recombinant protein therein was similarly obtained by ELISA assay as in the case of "X".

"Z1" represents a measurement value of the amount of the recombinant protein and was 0.0 in the processes (1) to (4) carried out using *Escherichia coli* (γ). In the processes, the supernatant solution collected in the process (4) was diluted with a Tris-NaCl buffer solution to an appropriate concentration and the amount of the recombinant protein therein was similarly obtained by ELISA assay as in the case of "X".

"Z2" represents a measurement value of the amount of the recombinant protein and was 1.1 in the processes (1) to (4) carried out using *Escherichia coli* (γ). In the processes, the sample prior to the centrifugation in the process (3) was treated with ultrasonic waves (200 W, 10 minutes) and the amount of the recombinant protein therein was similarly obtained by ELISA assay as in the case of "X".

The measurement values obtainable by ELISA assay were measured over a concentration range proportional to the amount of protein. The quantification value of the protein can be obtained from the measurement value of ELISA assay.

The secretion efficiency of *Escherichia coli* (α) in the case of using no surfactant was obtained from these measurement values of the amount of the protein using the following formula:

Secretion efficiency of *Escherichia coli* (α)=100× {(0.0/2.5)−(0.0/1.1)}=0.

<A-1>

*Escherichia coli* (α) and (β) were each cultured in the same manner as in the above case except that polyoxyethylene (3 mol) tridecyl ether sodium acetate as the surfactant (A) was added right after the resuspension of the *Escherichia coli* in the buffer solution in the process (3) of A-0, in an amount of 1% by weight on the basis of the weight of the suspension of the bacterium. The secretion efficiency was calculated according to the above-mentioned definition. Table 1 shows the results.

<A-2 to A-82>

With regard to *Escherichia coli* (α) and (β), the secretion efficiency was calculated in the same manner as in A-1 except that polyoxyethylene (3 mol) tridecyl ether sodium acetate in A-1 was changed to the surfactants shown in Table 1 or changed in the amount as shown in Table 1. Tables 1 to 3 show the results.

Here, in Tables 2 and 3, "0" indicates that the secretion efficiency was 0% and "–" indicates that the secretion efficiency was not measured.

The measurement of the secretion efficiency of *Escherichia coli* (β) was for confirmation that addition of the surfactant (A) makes *Escherichia coli* show a similar secretion efficiency even if the kind of the protein produced by *Escherichia coli* is changed. Measurement of the secretion efficiency of *Escherichia coli* (β) was conducted with regard to each of the cases in which the used surfactant (A) was A-1, A-3, or A-6.

TABLE 1

|  | Surfactant | The amount of surfactant (wt %) | Secretion efficiency (%) | |
|---|---|---|---|---|
|  |  |  | *Escherichia coli* (α) | *Escherichia coli* (β) |
| A-0 | — | — | 0 | — |
| A-1 | Polyoxyethylene(3 mol)tridecyl ether sodium acetate | 1 | 100.0 | 98.2 |
| A-2 | Palm oil fatty acid diethanol amide | 1 | 97.5 | — |
| A-3 | Palm oil fatty acid amide propyl dimethyl amino acetate betaine | 1 | 91.3 | 93.6 |
| A-4 | 1,2-dodecandiol monooxyethylene adduct | 1 | 90.7 | — |
| A-5 | Lauryl dimethylamino acetate betaine | 1 | 87.8 | — |
| A-6 | Cured palm oil fatty acid amidopropyl dimethyl aminoacetate betaine | 1 | 87.6 | 85.4 |
| A-7 | Sodium cocaminopropionate | 1 | 85.0 | — |
| A-8 | Sodium dodecyl diphenyl ether disulfonate | 1 | 79.1 | — |
| A-9 | Sodiumt polyoxyethylene (3 mol) laurylether acetate | 1 | 63.3 | — |

TABLE 1-continued

|  | Surfactant | The amount of surfactant (wt %) | Secretion efficiency (%) Escherichia coli (α) | Escherichia coli (β) |
|---|---|---|---|---|
| A-10 | EO 3 mol adduct of higher alcohol (C11 to C 15) | 1 | 56.9 | — |
| A-11 | Sodium polyoxyethylene (2.5 mol) laurylether sulfate | 1 | 53.2 | — |
| A-12 | EO 6 mol adduct of decyl alcohol | 1 | 53.1 | — |
| A-13 | Sodium N-lauroyl-N'-carboxymethyl-N'-hydroxyethyl ethylenediamine | 1 | 46.6 | — |
| A-14 | Cetyl trimethyl ammonium chloride | 1 | 37.8 | — |
| A-15 | Stearyl trimethyl ammonium chloride | 1 | 37.3 | — |
| A-16 | polyoxyethylene-p-isooctyl phenol | 1 | 36.7 | — |
| A-17 | Polyoxyethylene (3.7 mol) adduct of higher alcohol (48% of C14, 52% of C15) | 1 | 31.6 | — |
| A-18 | Triethanol amine alkyl (C12, C13) sulfate | 1 | 30.7 | — |
| A-19 | Dodecyl aminoethyl aminoethyl glycine hydrochloride | 1 | 29.6 | — |
| A-20 | Didecyl dimethylammonium chloride | 1 | 28.7 | — |
| A-21 | Dodecyl aminoethyl aminoethyl glycine | 1 | 28.2 | — |
| A-22 | Polyethylene glycol diisostearate | 1 | 26.2 | — |
| A-23 | 2-alkyl-N-carboxymethyl-N-hydroxyethyl imidazolinium betaine | 1 | 20.2 | — |
| A-24 | Polyoxyethylene (3 mol) lauryl ether acetate | 1 | 16.1 | — |
| A-25 | Ester thiodipropionate of polyoxyethylene (3 mol) alkyl (C12, C15) ether | 1 | 11.8 | — |
| A-26 | Stearylamine polyoxyethylene (15 mol) adduct | 1 | 11.0 | — |
| A-27 | 60% of isoalcohol monooleate, 20% of EO 10 mol adduct of cured castor oil, and 20% of EO 7 mol adduct of oleyl alcohol | 1 | 10.4 | — |
| A-28 | Lanolin fatty acid aminopropyl ethylene dimethyl ammonium ethyl sulfate | 1 | 9.2 | — |
| A-29 | Polyethylene glycol monoisostearate | 1 | 7.6 | — |
| A-30 | PO 3 mol and EO 5 mol adduct of higher alcohol (C12, C13) and 2-decyltetradecyl sodium phosphate | 1 | 6.3 | — |

TABLE 2

|  | Surfactant | The amount of surfactant (wt %) | Secretion efficiency (%) Escherichia coli (α) | Escherichia coli (β) |
|---|---|---|---|---|
| A-31 | Isostearylalcohol polyoxyethylene (5 mol) sodium phosphate | 1 | 6.2 | — |
| A-32 | Polyoxyethylene glyceryl triisostearate | 1 | 5.9 | — |
| A-33 | Polyoxyethylene (Mw = 190) stearic acid diester | 1 | 5.5 | — |
| A-34 | Polyoxyethylene isostearyl ether | 1 | 5.3 | — |
| A-35 | Polyoxyethylene (Mw = 200) oleate monoester | 1 | 5.3 | — |
| A-36 | Polyoxyethylene (added 14 mol each) block copolymer of polyoxypropylene glycol (Mw = 1700) | 1 | 5.2 | — |
| A-37 | Polyoxyethylene (20 mol) sorbitan monooleate | 1 | 5.2 | — |
| A-38 | Polyethylene glycol diisostearate | 1 | 5.1 | — |
| A-39 | EO 6 mol adduct of oleyl alcohol (46%), cetanol (32%), and octadecanol (22%) | 1 | 4.9 | — |
| A-40 | Polyethylene glycol monoisostearate | 1 | 4.9 | — |
| A-41 | EO 20 mol adduct of sorbitan trioleate | 1 | 4.6 | — |
| A-42 | Didecyl dimethyl ammonium adipate | 1 | 4.3 | — |
| A-43 | Sorbitan monooleate | 1 | 3.5 | — |
| A-44 | EO 25 mol adduct of cured castor oil | 1 | 3.0 | — |
| A-45 | EO 14 mol adduct of oleyl alcohol (46%), cetanol (32%), and octadecanol (22%) | 1 | 3.0 | — |
| A-46 | EO 5 mol adduct of oleyl alcohol (46%), cetanol (32%), and octadecanol (22%) | 1 | 2.9 | — |
| A-47 | Behenylamide propyldimethylamine | 1 | 2.8 | — |
| A-48 | Didecyl dimethyl ammonium chloride | 1 | 2.7 | — |
| A-49 | Sorbitan trioleate | 1 | 2.4 | — |
| A-50 | Distearyl dimethyl ammonium chloride | 1 | 2.3 | — |
| A-51 | PO 20 mol and EO 9 mol adduct of ethylhexanol | 1 | 2.3 | — |
| A-52 | Isostearyl alcohol polyoxyethylene (5 mol) adduct sodium ether carboxylate | 1 | 2.2 | — |
| A-53 | EO 4 mol adduct of oleyl alcohol (46%), cetanol (32%), and octadecanol (22%) | 1 | 2.0 | — |
| A-54 | Palm oil fatty acid sorbitan | 1 | 1.7 | — |
| A-55 | EO 10 mol adduct of cured castor oil | 1 | 1.7 | — |

TABLE 2-continued

| | Surfactant | The amount of surfactant (wt %) | Secretion efficiency (%) Escherichia coli (α) | Secretion efficiency (%) Escherichia coli (β) |
|---|---|---|---|---|
| A-56 | Polyoxyethylene (20 mol) sorbitan monolaurate | 1 | 1.6 | — |
| A-57 | Polyoxyethylene (Mw = 300) oleate diester | 1 | 1.5 | — |
| A-58 | Polyoxyethylene (Mw = 400) oleate monoester | 1 | 1.3 | — |
| A-59 | EO 10 mol adduct of oleyl alcohol | 1 | 1.1 | — |
| A-60 | EO 6 mol and PO 2.2 mol adducts of higher alcohol (48% of C14, 52% of C15) | 1 | 1.1 | — |

TABLE 3

| | Surfactant (A) | The amount of surfactant (wt %) | Secretion efficiency (%) Escherichia coli (α) | Secretion efficiency (%) Escherichia coli (β) |
|---|---|---|---|---|
| A-61 | EO 11 mol adduct of oleyl alcohol (46%), cetanol (32%), and octadecanol (22%) | 1 | 1.0 | — |
| A-62 | Polyhexamethylene biguanidine hydrochloride | 1 | 0.8 | — |
| A-63 | Oleic acid 4.5 mol ester of sorbitol EO 40 mol adduct | 1 | 0.7 | — |
| A-64 | EO 24 mol adduct trilaurate of trimethylolpropane | 1 | 0.5 | — |
| A-65 | Polyoxyethylene(10 mol)cetyl ether | 1 | 0.5 | — |
| A-66 | Polyoxyethylene(Mw = 1000)dioleate | 1 | 0.3 | — |
| A-67 | Polyoxyethylene(Mw = 600)oleate monoester | 1 | 0.3 | — |
| A-68 | 2-Ethylhexyl sodium sulfate | 1 | 0.2 | — |
| A-69 | Sodium lauryl sulfate | 1 | 0.0 | — |
| A-70 | EO 20 mol adduct of oleyl alcohol (46%), cetanol (32%), and octadecanol (22%) | 1 | 0.0 | — |
| A-71 | Bis(trimethylammonium methylene chloride)-alkyl(C9-15)toluene and mono(trimethylammonium methylene chloride)-alkyl(C9-15)toluene | 1 | 0.0 | — |
| A-72 | Polyoxyethylene(EO 20 mol)sorbitan monostearate | 1 | 0.0 | — |
| A-73 | 70% of dioctyl sodium sulfosuccinate, propylene glycol | 1 | 0.0 | — |
| A-74 | Lauryl diphenyl ether sodium disulfonate | 1 | 0.0 | — |
| A-75 | EO 9 mol and PO 2.2 mol adduct of higher alcohol(48% of C14, 52% of C15) | 1 | 0.0 | — |
| A-76 | EO 10 mol and PO 2.2 mol adduct of higher alcohol(48% of C14, 52% of C15) | 1 | 0.0 | — |
| A-77 | EO 13 mol and PO 2.2 mol adduct of higher alcohol(48% of C14, 52% of C15) | 1 | 0.0 | — |
| A-78 | EO 15 mol and PO 2.2 mol adduct of higher alcohol(48% of C14, 52% of C15) | 1 | 0.0 | — |
| A-79 | EO 17 mol and PO 2.2 mol adduct of higher alcohol(48% of C14, 52% of C15) | 1 | 0.0 | — |
| A-80 | EO 20 mol adduct of higher alcohol(48% of C14, 52% of C15) | 1 | 0.0 | — |
| A-81 | EO 39 mol adduct of higher alcohol(48% of C14, 52% of C15) | 1 | 0.0 | — |
| A-82 | sodium cholate | 1 | 0.0 | — |

The following surfactants were used in Tables 1 to 3.

A-16: Product of SIGMA

A-22: Product of Nihon Emulsion Co., Ltd. "EMALEX 400di-ISEX"

A-29: Product of Nihon Emulsion Co., Ltd. "EMALEX PE-12EX"

A-32: Product of Nihon Emulsion Co., Ltd. "EMALEX GWIS 320"

A-34: Product of Nihon Emulsion Co., Ltd. "EMALEX 1805"

A-38: Product of Nihon Emulsion Co., Ltd. "EMALEX 600di-ISEX"

A-40: Product of Nihon Emulsion Co., Ltd. "EMALEX PEIS-10EX"

Comparative Example 1

*Escherichia coli* (β) was inoculated in 10 mL of an LB culture medium and was shake-cultured at 37° C. overnight. In this manner, a culture solution was prepared. The strains were collected using a centrifuge and the collected *Escherichia coli* (β) strain was resuspended in 10 ml of a TB culture medium (product of Difco). Shake culture at 37° C. induced expression of torA. Sampling was performed after 0, 0.5, 1, and 2 hours from the start of the shake culture, and harvesting using a centrifuge was carried out for each sampled solution. Collected bacterial cells were suspended in a buffer solution (50 mM Tris (pH 7.5), 100 mM NaCl) and ultrasonic fragmentation was performed (200 W, 10 minutes). Then, an SDS-PAGE analysis was performed to quantify the produced recombinant protein band. Based on the obtained data, the protein amount per gram of the bacterial cell was calculated and a graph was constructed. FIG. 1 shows the results (without surfactant).

Example 1

The same processes were carried out as in Comparative Example 1 except that the surfactant A-7 was used as the surfactant (A) for the expression induction in an amount of 1% on the basis of the weight of the culture solution, and that sampling was performed after 0, 2, 4, 15, 19, and 21 hours from the initiation and analysis was performed on the supernatants of the centrifuged samples. A graph was similarly constructed. The dried cell density of the culture solution after 21 hours from the initiation was 1.72 g/L. FIG. 1 shows the results (with surfactant).

Production Example 4

A bglC gene of *Bacillus licheniformis* was amplified by the PCR method using primers 9 and 10 (Table 4). After being treated with restriction enzymes NcoI and BamHI, a PCR amplified fragment was bound to an NcoI restriction enzyme site and a BamHI restriction enzyme site of a pET-22b plasmid (product of Novagen). Then, the plasmid was transformed into a BL21 (DE3) *Escherichia coli* strain (product of Novagen) to form *Escherichia coli* (δ) that expresses cellulase.

Production Example 5

A subtilisin Carlsberg gene of a *Bacillus licheniformis* was amplified by the PCR method using primers 7 and 8 (Table 4). After being treated with restriction enzymes NcoI and BamHI, a PCR amplified fragment was bound to an NcoI restriction enzyme site and a BamHI restriction enzyme site of a pET-22b plasmid (product of Novagen). Then, the plasmid was transformed into a BL21 (DE3) *Escherichia coli* strain (product of Novagen) to form *Escherichia coli* (ε) that expresses protease.

TABLE 4

| Primer 1 | attaacatatgaaacaaagcactattgca (SEQ ID NO. 1) |
|---|---|
| Primer 2 | attaaggatccttatttcagccccagagc (SEQ ID NO. 2) |
| Primer 3 | attaacatatgaacaataacgatctc (SEQ ID NO. 3) |
| Primer 4 | attaaggatcctcatgatttcacctgcgac (SEQ ID NO. 4) |
| Primer 5 | attaacatatggttaaaacccaacgt (SEQ ID NO. 5) |
| Primer 6 | attaaggatcctcattgggtgttaacaatc (SEQ ID NO. 6) |
| Primer 7 | taataccatggcggctcagccggcg (SEQ ID NO. 7) |
| Primer 8 | taataggatccttattgagcggcagc (SEQ ID NO. 8) |
| Primer 9 | tggatccatggcgcagcttaccttaaaagg (SEQ ID NO. 9) |
| Primer 10 | ctgcaggatccttatttaggttcagtg (SEQ ID NO. 10) |

Comparative Example 2, Comparative Example 4

Overnight cultures (1 ml) of *Escherichia coli* (δ) obtained in Production Example 4 and *Escherichia coli* (ε) obtained in Production Example 5 were respectively prepared as Comparative Example 2 and Comparative Example 4. An amount of 0.5 ml of each was inoculated in 5 ml of an LB culture solution (containing 100 mg/L of ampicillin) and was shake-cultured at 30° C. for 3 hours. In this manner, pre-culture solutions were prepared. The pre-culture solutions were each inoculated in 50 mL of a culture solution (1.2 g of yeast extract (Nihon Pharmaceutical Co., Ltd.), 0.6 g of polypeptone (Nihon Pharmaceutical Co., Ltd.), 0.47 g of dipotassium phosphate, 0.11 g of monopotassium phosphate, 0.35 g of ammonium sulfate, 0.66 g of disodium phosphate 12-hydrate, 0.02 g of sodium citrate dihydrate, 0.2 g of glycerol, 1.5 g of lactalbumin hydrolysate, 0.3 g of a defoaming agent (Shin-Etsu Chemical Co., Ltd., "KM-70"), 1 mM magnesium sulfate, trace metal solution (18.9 μg of calcium chloride, 500 μg of iron chloride (III), 9.0 μg of zinc sulfate heptahydrate, 5.1 μg of copper sulfate, 6.7 μg of manganese chloride tetrahydrate, 4.9 μg of cobalt chloride, 200 μg of ethylene-diamine-tetraacetic acid tetrasodium salt), 100 mg/L ampicillin). Culturing was initiated with use of a microbial culture system (ABLE Corporation, product name "BioJr. 8"), while the pH value and the temperature were maintained at 6.8 and 30° C. After the culturing was initiated, 0.15 mL of 1M IPTG was added. After 14 hours from the initiation of culturing, instillation of a glycerin/protein solution (50% of glycerin, 50 g/L of lactalbumin hydrolysate, a 33 g/L defoaming agent (Shin-Etsu Chemical Co., Ltd., "KM-70"), 100 mg/L ampicillin) was started. The culturing was terminated after 48 hours from the initiation and the culture solution was recovered. The whole protein in the culture solution was analyzed by SDS-PAGE. Based on the obtained amount of the protein band, the recombinant protein was quantified.

<Measurement of Dried Cell Density>

The dried cell density at the termination of the culturing was determined by the following processes (1) to (5):

(1) measuring the weight of the container (centrifuge tube) in advance;

(2) charging 100 ml of a culture solution into the container weighed in the process (1), centrifuging the culture solution (4000 G, 15 minutes, 4° C.), and collecting the bacteria by removing the supernatant;

(3) washing the collected bacteria with a 0.9% NaCl aqueous solution [same volume as the culture solution used in the process (2)], centrifuging the solution again (4000 G, 15 minutes, 4° C.), and collecting the bacteria by removing the supernatant;

(4) drying the bacteria obtained in the process (3) in the container at 105° C. for 10 hours, and measuring the total weight of the container and the bacteria; and (5) further drying the bacteria at 105° C. for 2 hours after the process (4) and measuring the total weight of the container and the bacteria to confirm that no weight change was observed, and if the weight was further reduced, continuing the drying at 105° C. until the weight change was not observed.

The dried cell density was determined by applying the measuring results in the process (5) and the process (1) and the volume (L) of the culture solution used in the process (2) to the following formula:

$$\text{Dried cell density (g/L)} = ([\text{measuring result in process (5)}] - [\text{measuring result in process (1)}])/0.1.$$

Performance of this processes for several times clarified the proportional relationship between the turbidity of the culture solution and the dried cell density. Therefore, the dried cell density was obtained from the measured turbidity in each of Comparative Examples 2 to 4 and Examples 2 to 14.

<Measurement of Turbidity of Culture Solution>

The turbidity of a culture solution that is same as the culture solution used in the measurement of the dried cell density was measured using a turbidimeter (Shimadzu Corporation, UV-1700) and 1 ml of quarts cell.

For measurement, the culture solution was diluted in saline to have an appropriate absorbance. The absorbance of the same culture solution (but not containing bacteria) diluted at the same dilution as above was set as a blank. The turbidity of the culture solution was calculated by using the following formula:

Turbidity of culture solution=[(measured turbidity of diluted culture solution)−(measured turbidity of blank)]×dilution rate.

Figure 3:
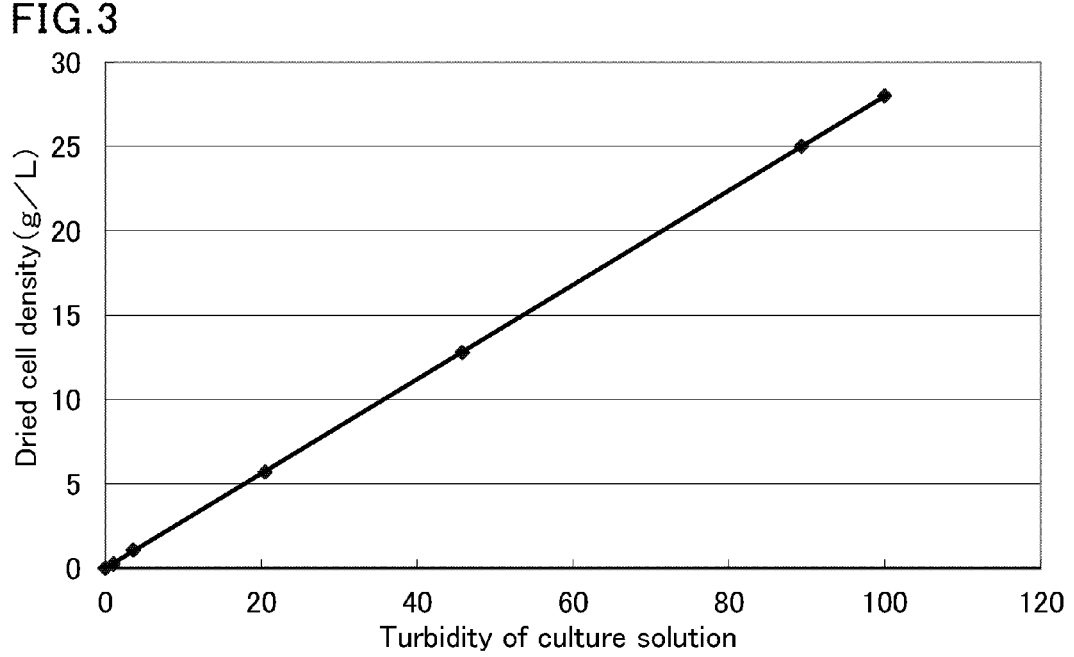
FIG. 3 is a graph showing a proportional relationship between the turbidity and the dried cell density of a culture solution, and is used for obtaining a formula for calculating the dried cell density from the turbidity of the culture solution.

The dried cell density and the turbidity of the culture solution were plotted to construct a graph in FIG. 3. Based on FIG. 3, the following formula indicating a relationship between the dried cell density and the turbidity of the culture solution was obtained:

Dried cell density=0.28×(turbidity of culture solution).

Comparative Example 3

The same processes as in Comparative Example 2 were carried out except that, after culturing was initiated, the surfactant A-14 was added as the surfactant (A) to the culture solution in an amount of 1% by weight on the basis of the weight of the culture solution and was also added to the glycerin/protein solution in an amount of 1% by weight on the basis of the weight of the glycerin/protein solution.

Example 2

The same processes as in Comparative Example 2 were carried out except that, after culturing was initiated, the surfactant A-14 was added as the surfactant (A) to the culture solution in an amount of 1% by weight on the basis of the weight of the culture solution and was also added to the glycerin/protein solution in an amount of 1% by weight on the basis of the weight of the glycerin/protein solution, and that the analysis was performed only to the supernatant obtained by centrifugation of the culture solution. Here, the time between the initiation of the culturing and the addition of the surfactant was longer than that in Comparative Example 3.

Examples 3 to 11

Quantification of the recombinant protein obtained and measurement of the dried cell density were carried out in the same manner as in Example 2 except that the surfactant A-14 was changed to the surfactants shown in Table 5 or changed in the amount as shown in Table 5. Table 5 shows the results.

Example 12

The same processes as in Comparative Example 4 were carried out except that, after culturing was initiated, the surfactant A-6 was added as the surfactant (A) to the culture solution in an amount of 1% by weight on the basis of the weight of the culture solution and was also added to the glycerin/protein solution in an amount of 1% by weight on the basis of the weight of the glycerin/protein solution, and that the analysis was performed only to the supernatant obtained by centrifugation of the culture solution.

Example 13

The same processes as in Comparative Example 4 were carried out except that, after culturing was initiated, the surfactant A-6 was added as the surfactant (A) to the culture solution in an amount of 0.1% by weight on the basis of the weight of the culture solution and was also added to the glycerin/protein solution in an amount of 0.1% by weight on the basis of the weight of the glycerin/protein solution, and that the analysis was performed only to the supernatant obtained by centrifugation of the culture solution.

Example 14

The same processes as in Comparative Example 4 were carried out except that, after culturing was initiated, the surfactant A-6 was added as the surfactant (A) to the culture solution in an amount of 5% by weight on the basis of the weight of the culture solution and was also added to the glycerin/protein solution in an amount of 5% by weight on the basis of the weight of the glycerin/protein solution, and that the analysis was performed only to the supernatant obtained by centrifugation of the culture solution.

Figure 2:
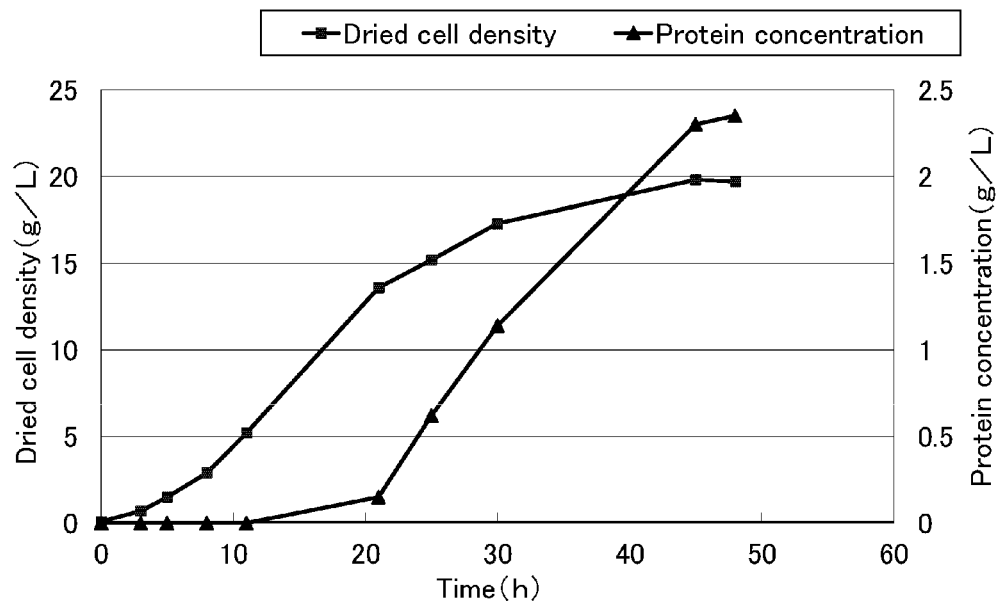
FIG. 2 is a graph showing the time course of the dried cell density of a culture solution and the concentration of a produced recombinant protein with regard to the results of Example 7.

With regard to Example 8, sampling was performed after 3, 5, 8, 11, 21, 25, 30, 45, and 48 hours from the addition of the surfactant A-6. Using the samples, the dried cell density and the quantity of the recombinant protein were determined. FIG. 2 shows the results.

TABLE 5

| | | Surfactant (A) | The amount of surfactant (wt %) | Turbidity | Dried cell density (g/L) | Bacterium | Quantitative value of produced recombinant protein (g/L) |
|---|---|---|---|---|---|---|---|
| Comparative | 2 | — | 0 | 87.5 | 24.5 | Escherichia coli(δ) | <0.05 |
| Example | 3 | A-14 | 1 | 1.07 | 0.3 | Escherichia coli(δ) | <0.05 |
| | 4 | — | 0 | 85 | 23.8 | Escherichia coli(ε) | <0.05 |
| Example | 2 | A-14 | 1 | 5.43 | 1.52 | Escherichia coli(δ) | 0.06 |
| | 3 | A-76 | 1 | 84.3 | 23.6 | Escherichia coli(δ) | 0.07 |
| | 4 | A-60 | 1 | 66.4 | 18.6 | Escherichia coli(δ) | 0.1 |
| | 5 | A-17 | 1 | 82.9 | 23.2 | Escherichia coli(δ) | 0.35 |
| | 6 | A-13 | 1 | 76.4 | 21.4 | Escherichia coli(δ) | 1.79 |
| | 7 | A-7 | 1 | 78.9 | 22.1 | Escherichia coli(δ) | 2.24 |
| | 8 | A-6 | 1 | 70.3 | 19.7 | Escherichia coli(δ) | 2.35 |
| | 9 | A-5 | 1 | 85 | 23.8 | Escherichia coli(δ) | 2.58 |
| | 10 | A-9 | 1 | 50.7 | 14.2 | Escherichia coli(δ) | 1.35 |
| | 11 | A-1 | 1 | 43.2 | 12.1 | Escherichia coli(δ) | 1.01 |

TABLE 5-continued

| | Surfactant (A) | The amount of surfactant (wt %) | Turbidity | Dried cell density (g/L) | Bacterium | Quantitative value of produced recombinant protein (g/L) |
|---|---|---|---|---|---|---|
| 12 | A-6 | 1 | 95 | 26.6 | Escherichia coli(ε) | 0.37 |
| 13 | A-6 | 0.1 | 75.2 | 21.1 | Escherichia coli(δ) | 1.82 |
| 14 | A-6 | 5 | 52.1 | 14.6 | Escherichia coli(δ) | 1.53 |

Comparative Example 5

An overnight culture solution (10 ml) of Shewanella putrefaciens was prepared and inoculated in 1 L of a culture solution (10 g of polypeptone (Nihon Pharmaceutical Co., Ltd.), 2 g of yeast extract (Nihon Pharmaceutical Co., Ltd.), 0.5 g of magnesium sulfate heptahydrate, 750 mL of Seawater (Daigo)) and was shake-cultured at 30° C. for 5 hours. In this manner a pre-culture solution was prepared. The pre-culture solution was inoculated in 10 L of a culture solution (200 g of polypeptone (Nihon Pharmaceutical Co., Ltd.), 40 g of yeast extract (Nihon Pharmaceutical Co., Ltd.), 10 g of magnesium sulfate heptahydrate, 7.5 L of Seawater (Daigo)). Culturing thereof was initiated with use of a microbial culture system (ABLE Corporation), while the pH value and the temperature were maintained at 7.3 and 30° C. After 48 hours from the initiation of culturing, the culture solution was recovered and centrifuged. The whole protein of the obtained supernatant fragment was analyzed by SDS-PAGE and the protein band around 45 kDa was quantified.

<Measurement of Dried Cell Density>

The dried cell density when the culturing is terminated was determined by the following processes (1) to (5):

(1) measuring the weight of the container (centrifuge tube) in advance;

(2) charging 100 ml of a culture solution into the container of the process (1), centrifuging the culture solution (4000 G, 15 minutes, 4° C.), and collecting the bacteria by removing the supernatant;

(3) washing the collected bacteria with a 0.9% NaCl aqueous solution [same volume as the culture solution used in the process (2)], centrifuging the solution again (4000 G, 15 minutes, 4° C.), and collecting the bacteria by removing the supernatant;

(4) drying the bacteria obtained in the process (3) in the container at 105° C. for 10 hours, and measuring the total weight of the container and the bacteria; and (5) further drying the bacteria at 105° C. for 2 hours after the process (4) and measuring the total weight of the container and the bacteria to confirm that no weight change was observed, and if the weight was further reduced, continuing the drying at 105° C. until the weight change was not observed.

The dried cell density was determined by assigning the measuring results in the process (5) and the process (1) and the volume (L) of the culture solution used in the process (2) to the following formula:

Dried cell density (g/L)=([measuring result in process (5)]−[measuring result in process (1)])/0.1.

Comparative Example 6

The same processes as in Comparative Example 5 were carried out except that, after culturing in the microbial culture system was initiated, the surfactant A-14 was added to the culture solution in an amount of 1% by weight on the basis of the weight of the culture solution.

Example 15

The same processes as in Comparative Example 5 were carried out except that, after culturing in the microbial culture system was initiated, the surfactant A-7 was added to the culture solution in an amount of 1% by weight on the basis of the weight of the culture solution.

TABLE 6

| | | Surfactant (A) | The amount of surfactant (wt %) | Dried cell density (g/L) | Bacterium | Quantitative value of produced recombinant protein (g/L) |
|---|---|---|---|---|---|---|
| Comparative Example | 5 | — | 0 | 2.84 | Shewanella | <0.01 |
| Comparative Example | 6 | A-14 | 1 | 0.23 | Shewanella | <0.01 |
| Example | 15 | A-7 | 1 | 2.32 | Shewanella | 0.04 |

As illustrated in FIG. 2, the dried cell density prior to the addition of the A-6 surfactant was 2.3 g/L and the dried cell density when the culturing was terminated was 19.7 g/L in Example 8. This indicates that at least a part of the bacterium used in the culturing was not killed and kept growing.

The surfactant to be used in production by secretion by Escherichia coli was determined based on the screening results (Tables 1 to 3) of the secretion efficiency calculated using Escherichia coli (α), (β), and (γ).

Tables 1 to 3 show that the secretion efficiency is 1 or more when any of the A-1 to A-61 surfactants was used among all the surfactants. These surfactants allow efficient elution of a protein in the periplasm of Escherichia coli and were expected to show highly effective performance in the production by secretion. In Examples 1 to 15, the productivity of the production by secretion was confirmed using a plurality of kinds of surfactants.

As a result, more efficient secretion of the produced protein into the culture solution was confirmed in Examples 2 to 14 of the present invention, compared to Comparative Examples 2 and 4 in which no surfactant was used, as shown in Table 5.

In FIG. 1 showing the time course of the protein production per gram of bacterial cells at each time interval, the amount of the protein was hardly changed after 1 hour or more from the initiation of culturing when no surfactant was used. In contrast, when a surfactant was used, the amount of the protein kept increasing even after 15 hours from the initiation of culturing.

FIG. 2 in which the dried cell density of the culture solution and the protein amount are plotted indicates that bacteria were not killed and kept growing and producing the protein even in the presence of the surfactant of the present invention in Example 8.

These results indicate that use of a surfactant enabled the production of the protein by secretion for a long time without disturbing the protein production by the bacteria and allowed the produced protein to be efficiently isolated into the culture solution. This led to the production of the protein in a larger volume.

Comparison between Comparative Example 3 and Example 2 clarifies that a larger dried cell density results in a larger production volume of the protein when the bacterium and the surfactant used in the production by secretion are not changed.

Moreover, comparison of Examples 3 to 9 clarifies that the production volume of the protein is larger in Examples in which the secretion efficiency of the surfactant is larger.

It is to be noted that, in the present description, the secretion efficiency of "0.0" does not necessarily mean that an intracellular useful substance is not at all secreted extracellularly (into the culture solution). For example, though the surfactant A-76 which allows Escherichia coli (δ) to have secretion efficiency of "0.0" was used in Example 3, the amount of the recombinant protein secreted by Escherichia coli (δ) was 0.07 g/L.

INDUSTRIAL APPLICABILITY

The surfactant and the method for producing a useful substance of the present invention can be used in extraction of a useful substance such as protein from a producing bacterium. Examples of the protein include enzymes, hormonal proteins, antibodies, and peptides. When the produced protein is an enzyme (protease, cellulase, lipase, amylase, etc.), the enzyme is suitably used in food processing, detergents, fiber treatment, paper manufacturing, enzyme conversion, and the like.

Moreover, the surfactant of the present invention is also usable as an extracting reagent for extracting periplasmic fraction of bacteria.

The invention claimed is:

1. A method for producing a substance, comprising: culturing a bacterium in a culture solution comprising a surfactant mixed therein, wherein said substance is synthesized by said bacterium and said substance is secreted into the culture solution by said bacterium, and maintaining said bacterium in the culture solution at a dried cell density of 1.5 to 500 g/L based on a volume of the culture solution, wherein said surfactant is at least one surfactant selected from the group consisting of polyoxyethylene (3 mol) tridecyl ether sodium acetate, palm oil fatty acid amide propyl dimethyl amino acetate betaine, lauryl dimethylamino acetate betaine, cured palm oil fatty acid amidopropyl dimethyl aminoacetate betaine, sodium cocaminopropionate, sodium polyoxyethylene (3 mol) laurylether acetate, sodium polyoxyethylene (2.5 mol) laurylether sulfate, and sodium N-lauroyl-N'-carboxymethyl-N'-hydroxyethyl ethylenediamine, wherein said substance is a protein, and wherein said bacterium is a gram negative bacterium.

2. The method for producing a substance according to claim 1, wherein said protein secreted by said gram negative bacterium is translocatable to a periplasm of the gram negative bacterium.

3. The method for producing a substance according to claim 1, wherein said gram negative bacterium is *Escherichia coli*.

4. The method for producing a substance according to claim 1, wherein an amount of said surfactant in the culture solution is 0.0001% to 10% by weight based on the weight of the culture solution.

* * * * *